United States Patent [19]

Hadwiger et al.

[11] Patent Number: 5,312,912
[45] Date of Patent: May 17, 1994

[54] PROCEDURES AND REGULATORY DNA SEQUENCES FOR GENETICALLY ENGINEERING DISEASE RESISTANCE AND OTHER INDUCIBLE TRAITS IN PLANTS

[76] Inventors: Lee A. Hadwiger, Dept. of Plant Pathology, Washington State University, Pullman, Wash. 99164; Chin C. Chiang, P.O. Box 2884 CS, Pullman, Wash. 99165; Daniel A. Horovitz, Rte. 1, Box 159, Palouse, Wash. 99161

[21] Appl. No.: 393,301

[22] Filed: Jun. 13, 1989

[51] Int. Cl.$^5$ .................. C12N 15/11; C12N 15/29
[52] U.S. Cl. ...................... 536/24.1; 435/320.1; 935/30; 935/35
[58] Field of Search ........... 536/27; 435/172.3, 172.1, 435/320.1; 935/30.35; 800/205

[56] References Cited

PUBLICATIONS

Curran et al (Nov. 4, 1988) Cell 55: 395–397.
Cornelissen et al. (1986) The EMBO Journal 5(1): 37–40.
Cockerill et al (1987) J. Biol Chem 262 (11): 5394–5397, Abstract 24821, Biological Abstracts Aug. 1, 1987.
Fristensky et al (Dec. 1988) Plant Molecular Biology 11: 713–715.
Fristensky et al (1985) Physiological Plant Pathology 27: 15–28.
Daniels et al (1987) Plant Molecular Biology 8: 309–316.
Daniels et al in *Plant Gene Systems and their Biology*, Alan R. Liss, Inc. 1987, pp. 161–170.

*Primary Examiner*—Elizabeth C. Weimar
*Assistant Examiner*—C. Chereskin

[57] ABSTRACT

Novel DNA sequences have been acquired from pea plants which are central in the defense of pea plants against root rotting pathogens and other pathogens of plants species such as potato pathogen. A method is described for protecting dicaryotic plants (e.g. potato) transformed with reconstructions of these seqeunces which utilize the unique nature of their promoter (regulatory DNA sequence) sequences to enable them to respond to pathogen challenge in transgenic plants. This manipulated response resulting from expression of the coded structural gene assists in maintaining host cell viability and thus assists disease resistance.

1 Claim, 15 Drawing Sheets

FIGURE 1A

```
-1084  GTCGACACATATGTAAACAGGTCGGCCTATAGTAAATCTA
                 ‾‾‾‾‾‾‾‾‾‾‾‾‾‾‾‾
                        ↑
-1044  ATAAATCCTCAAGATATATGTAACTACTAATCTTGATGTC
                      ‾‾‾‾‾‾‾‾‾‾‾‾‾‾‾‾    ‾‾‾
                             ↑
-1004  AACATTTCTCCACACATCTTGATTTGACTCACCAGTCTTG
       ‾‾‾‾‾‾‾‾‾‾              ‾‾‾‾‾‾‾‾
           ↑                       a
 -964  TTACCCTAGTGAAGAAATCAACGATGCTTTCACCTTCTTG

-924  TTCCTCACTCGTTACTAGAGTGATTCAACCACACCTTGAT

-884  TGGAAAATGGTTTCACCTCACAATGATTTGAAAAGAAAAG

-844  AATTATGTGAAAGTGAATTGAGAAGATAAGAGAAATTAG
                              →→→→→→→→→→→→
                              ‾‾‾‾‾‾‾‾‾‾‾‾‾
 -804  GATTTAGGGAGAAAGAGAAGAAGATTGATCAAATTCTGCA
              →→→→→→→→→
              ‾‾‾‾‾‾‾‾‾‾‾‾‾‾‾‾
 -764  GATTTCTCTTTGTGTTTTATTCCAACTGAACTTCCATTC

-724  TTTTTAACTACTTTACAACAGTAAGTTACCTCGCTATTTA

-684  TAGATGATATTACTTACACACCTAGTAATCTCGAACTAAT

-644  TCAACTAATAAATACTAATTTTTAACTTTGACGAGGTTAA
 -564  TTCGACTATTAATTTATCGAATACATTCGACTTTGACTTT
 -604  CTCCTTCGACAACTACTTACTTCAATTGTTTAAGACTATA
 -524  ATTGAATCTTACATACATGCTTAACACAAATAATTACATA
 -484  TTTAACTTTTTTTTTTCTCCATCTCTCTTTACTATATTAA
 -444  ATAATGTGAAATAATATAAATACTGTTTAACATGTTTTAT
 -404  TTCAATATCCCAATACTGACCTCAAACTCAAAATTTAGAA

-364  GAAAAAGAACTAGCAACAACATAATTTGTATGAATAGAC
                                   →→→→→→→    ←
 -324  GTAACCTAGTTTTTCACAAAATAACCAGTTAAATTTAACT
                                 ‾‾‾‾‾‾‾‾‾‾‾‾‾‾
```

FIGURE 1B

```
-284  GTTTATATATTTAAGTGATAATCATTTATCTCGGATTCTT

-244  TACTCGACACAAATGAGTTAAGATGAGTATATGTTAGTTT

-204  TGGTAAAAATGTATAATTTAGTTAGATATATGTTTAATT
                     Z
-164  TGAGTAGGATATGTTGGCACGCACGAACCAAATACGTATA
                                          Z
-124  GGAACGTGGATAAAAATAATACTATTGACCAAATGCATAT
                     e
 -84  CAGAACGTGAATACAAAATGGTCCAGCGACTTGGTATTAA

-44  TAGCTATACAATGCATCTTCATTTCTTATAAATAGAACTT

-4  CAACTCCACTCGTAAATCACACAGCTAGGCAAGCACCTTC
  36  TTATTTATAGCATTATAAATCATCATTATCATGGGTGTTT
                                       METGLYVALP

76  TCAATTTTGAGGAAGAAGCCACTTCCATTGTAGCTCCTGC
      HEASNPHEGLUGLUGLUALATHRSERILEVALALAPROAL

116  TACACTTCACAAAGCTCTGGTTACAGATGCTGACATTCTT
      ATHRLEUHISLYSALALEUVALTHRASPALAASPILELEU

156  ACTCCAAAGGTTATTGATGCCATCAAAAGTATTGAAATTG
      THRPROLYSVALILEASPALAILELYSSERILEGLUILEV

196  TTGAAGGAAACGGTGGCCCCGGAACCATCAAGAAACTCAC
      ALGLUGLYASNGLYGLYPROGLYTHRILELYSLYSLEUTH

236  TTTCGTTGAAGGTCAGTATTAGAATATTCTTTTCATGATA
      RPHEVALGLUA

276  TATCATTATTACTAGTATTATTGTTTATGATTGTGAAATG
 316  AATCAATTGTGTGTTGCAGACGGTGAAACCAAGTATGTGT
                        SPGLYGLUTHRLYSTYRVALL

356  TACACAAAGTGGAGTTAGTAGATGATGCTAACTGGGCAAA
      EUHISLYSVALGLULEUVALASPASPALAASNTRPALAAS
```

FIGURE 1C

```
396  CAACTACAGCATAGTTGGAGGTGTTGGACTTCCGGACACA
     NASNTYRSERILEVALGLYGLYVALGLYLEUPROASPTHR

436  GTTGAGAAGATCTCGTTTGAGGCTAAATTGTCTGCAGGAC
     VALGLULYSILESERPHEGLUALALYSLEUSERALAGLYP

476  CAAATGGAGGATCCATTGCAAAGCTGAGTGTGAAATATTA
     ROASNGLYGLYSERILEALALYSLEUSERVALLYSTYRTY

516  TACCAAGGTGATGCTATTCCTAGTGAAGAGGAAATCAAG
     RTHRLYSGLYASPALAILEPROSERGLUGLUGLUILELYS

556  AATGGCAAAGCCAAAGGTGAAGGTATTTTCAAGGCTCTTG
     ASNGLYLYSALALYSGLYGLUGLYILEPHELYSALALEUG

596  AAGGTTACTGTGTGGCTAATCCTGATTACAACTAAAAAAT
     LUGLYTYRCYSVALALAASNPROASPTYRASNEND

636  TTAATTAAGTGAGTGCTTGTTTTATTATGGTGTGTTATGA

676  CACATTTATTGCATCTGTCGGCTTAATTTGTTTTCTTAT

716  TTTCTTTCTTTTCCCTTTCCTATTGTTGAGGAAGTGTGA
756  GTTTGAGATTGTAAGTCATGTTTGTACCACGTTTTAAGAA
796  ATTATAATAATACGTATGTTCTTTTTTATATATTTTTTTT
836  TCTCTAGAAAATATTGTTACTAAAACAAAATTGTTACTAA
876  AAAACATTTAAAATATTGGTAGGGATTTGATACCACCAAT

916  GTAAACCATTGAAATGAAGATCCAAAACGTGACTACTTTG
                ↑

956  ATTGTTTTGGTAATAAAATAAAAAATTTCAATCACACCAA
           ↑

996  AAAAATTTAATTTGTATATAACTAAAATAAATAATCTTCT
1036 ACAGAACAATAACAAGATAAAATACAAAAAAACACAATAA
1076 TTTGTGTACTCAGTTCGATCAAAAAAATCTACTCTAAAGG
          a
```

FIGURE 1D

1116 TAAGAAAAACTCTGAGTCATTATACTTCCTATTGTGGGCC

1156 GACCAAAGTCAATCCAAGAGTCCAACCAGAGTCAGACCAA

1196 TCAAGGATCC

FIGURE 2A

-729 TCGAGTTTGAATATTGTGTTTAATAAATTTATACAGAGTT

-689 TCGTTTGATTTTATTTAAATCTTCTAGATATTGAGTTGAG

-649 TTACTCAATAAATTTTTGCTCCGTCTTCCATTGAATTTT

-609 TCGGTCATAAGGGTTAAGTAGTTAAAAAAAGAAAATAAT

-569 TATGACAGAGATATTGAGTTGTTAATATATATATATATAT

-529 ATATATATATATATATATATATATATATATATATATATAT

-489 ATATATATATATATTTTTTTTGTGTGTGTGAAAATTTAA

-449 AAAATAAAGAA GTAAGTANNNNNN - Gap - TATAA

-419 TTAAAATATTTTATAAATCGGATAACTCATCGGTCTACAA

-379 ATCAATTTTGTAGAGTTGAATTACATTCGATCACATTTTT

-339 AAAATATATATTTTTTAAATTAAATTTAATATTTTTGGAG

-299 ATAAAACATTAGTATTAACTAAAATTCTATACAATTAACT

-259 AATTTGAGAAAAAATTAATTAATAGATCACATAGCCACCT

-219 TACCTCATTGGACTAAACGTCAAGGTCTTCTAAGAGAATT

FIGURE 2B

```
-179  TGAGTTACATCACACCCCAAAATTTTAATTTAATAAATAT

-139  TTATTATATTTGTCTTATATATCTTACAATTTTTTATTAG
 -99  ATTCTTTGAAAGAAAAATAAATAAGTTTGAATTGTTTTCA
 -59  AATAAATTAAATTAAGATTTTTCTTCTTCTCTTATAAAAG
 -19  GGCAATACAACCATAGTCTAAACCAAATCCTTCCACTCCT
  21  TCTTTACTTTCAAGTTCCAATAGCTAAGTAATAAAATGGG
                                        METGL

61  TTCCAAACTTCCAGTACTGTTTGTTTTTGTGATGTTGTTT
      YSERLYSLEUPROVALLEUPHEVALPHEVALMETLEUPHE

101  GCTTTAAGTTCAGCCATTCCAAACAAGAGAAAGCCATATA
      ALALEUSERSERALAILEPROASNLYSARGLYSPROTYRL

141  AACCATGCAAAACCTAGTCCTTTATTTTCATGATATACT
      YSPROCYSLYSASNLEUVALLEUTYRPHEHISASPILELE

181  TTACAATGGAAAGAATGCAGCAAATGCAACATCAGCAATA
      UTYRASNGLYLYSASNALAALAASNALATHRSERALAILE

221  GTAGCAGCTCCAGAAGGTGTTAGTTTAACTAAATTGGCAC
      VALALAALAPROGLUGLYVALSERLEUTHRLYSLEUALAP

261  CTCAATCCCACTTTGGTAACATAATAGTTTTTGATGACCC
      ROGLNSERHISPHEGLYASNILEILEVALPHEASPASPPR

301  TATCACATTAAGCCATAGCCTTTCTTCAAAACAAGTTGGA
      OILETHRLEUSERHISSERLEUSERSERLYSGLNVALGLY

341  AGAGCACAAGGGTTTTATATTTATGATACCAAAAACACAT
      ARGALAGLNGLYPHETYRILETYRASPTHRLYSASNTHRT

381  ACACTTCTTGGCTTAGTTTCACTTTTGTTCTTAATAGCAC
      YRTHRSERTRPLEUSERPHETHRPHEVALLEUASNSERTH

421  TCATCATCAAGGAACCATTACTTTTGCTGGAGCTGACCCA
      RHISHISGLNGLYTHRILETHRPHEALAGLYALAASPPRO
```

FIGURE 2C

```
461  ATTGTCGCCAAAACTAGAGATATTTCTGTCACTGGTGGTA
     ILEVALALALYSTHRARGASPILESERVALTHRGLYGLYT

501  CTGGAGATTTCTTTATGCATAGAGGAATTGCTACTATTAC
     HRGLYASPPHEPHEMETHISARGGLYILEALATHRILETH

541  CACTGATGCCTTTGAAGGCGAGGCTTATTTTCGACTTGGT
     RTHRASPALAPHEGLUGLYGLUALATYRPHEARGLEUGLY

581  GTTTACATCAAGTTCTTTGAGTGTTGGTAACTATCAAATT
     VALTYRILELYSPHEPHEGLUCYSTRPEND

621  AAGTACTACTTGCTATAGTAAAACCAATTAAATTTGAAGT

661  TAAATTGTTGTTGTCTCTTTTCATGTTGTGTTTTTAATT

701  AATTAGCCCAGAAAGTATACTTTGTACTTTTTTATTCTCT

741  AAGATTATTATCAATAAATGAAGATTCTATTAACTATTTT

781  CTTTTTTTAGAATAAGCATATCACTTTTTCATATTGACTT

821  ATAAGATAAATAAATTCTTGTCAATATTATTTTTCAAACA

861  ACACAAAAATTATAAATGACATTGAATCGACATAAGTAGC

901  TAAGCACACACATGTAAATGAAACCGTGTAGGAGGATTGG
941  AAGAGTTATTAGCTGAAGTGGATGAGGATTGAGTCTGACA
981  GTTACTATTTTCCTAGTCTAAAAGTCCATGGCAAACACCA
1021 TGAGTGCAAAACTGGTTAACGTGGGTATAACTCAAATCA
1061 AATAATCTCAACAATTTCTTTTCTTCAAATCCTCACATCT
1101 AAAGCTTGTGACGAAAATTAATCATAAATGATATCTCTTT
1141 GTACTTCTTTTGTTCTCTGT
```

PROCEDURES AND REGULATORY DNA SEQUENCES FOR GENETICALLY ENGINEERING DISEASE RESISTANCE AND OTHER INDUCIBLE TRAITS IN PLANTS

STATEMENT AS TO RIGHTS TO INVENTIONS MADE UNDER FEDERALLY SPONSORED RESEARCH AND DEVELOPMENT

This invention was made with Governmental support under grant RX-18 awarded by the Washington Sea Grant program. The Government has certain rights in this invention.

BACKGROUND OF THE INVENTION

This invention relates to a method for transferring DNA sequences, including a description of the unique DNA sequences, capable of transferring non-host resistance between plant species.

Through evolution only a relatively small group of microorganisms have found their pathological niche on a given plant species. Fortunately, the same niche is not usually available for this same microbe group in a different plant species. Thus, the "different" plant species is said to express "non-host" resistance (Heath, M. C. Non-host resistance in: Plant Disease Control; Resistance and Susceptibility. R. C. Staples and G. H. Toehniessen, Eds. John Wiley and Sons, Inc., New York, p. 201, 1981.) to this group of microorganisms. This mismatch is often manifest as an intense host plant response (hypersensitive response) based on the activation of a selection of host genes (Daniels, C. H., Fristensky, B. W., Wagoner, W. W. and Hadwiger, L. A. Pea genes associated with non-host disease resistance to Fusarium are also active in race-specific disease resistance to Pseudomonas. Plant Molecular Biology, 8, 309, 1986; Fristensky, B. W., Riggleman, R. C., Wagoner, W. W. and Hadwiger, L. A. Gene expression in susceptible and disease resistant interactions of peas induced with *Fusarium solani* pathogens and chitosan. Physiol. Plant Pathol., 27, 15, 1986.). Non-host resistance has recently attained a new importance with the advent of genetic engineering, because it is now possible to transfer genes from a species which actively resists a given plant pathogen to a species which is infected by that pathogen (Hadwiger, L A., Chiang, C. C., Pettinger, A., and Chang, M. M. Strategy to improve disease resistance by transferring "non-host" disease resistance genes from peas to potatoes. University of Maryland—USDA—DuPont, 2nd Int'l. Symp. on Biotechnology and Food Safety, Butterworth, Boston, 1990.). Theoretically, there is a limitless source of potential disease resistance genes existing in all of the plant species on earth, this invention describes a method for transferring specific DNA sequences from a pea (*Pisum sativum*) plant to transformable plant species such as tobacco and potato. it defines the state of knowledge of how these genes are controlled and defines a combination of genes needed to code for that portion of the intense host response which actually suppresses the pathogen and preserves the viability of host cells (Kendra, D. F. and Hadwiger, L A. Cell death and membrane leakage not associated with the induction of disease resistance in peas by chitosan or *Fusarium solani* f. sp. *phaseoli,* Phytopathol., 77, 100, 1987.) adjacent to the point of pathogen challenge. Conventional plant breeding techniques have used pathogen race-specific genes (Fehr, W. R. Principals of cultivar development. V. 1, Ch.21, Breeding for pest resistance. MacMillan Pub. Co., N.Y., 304–13. 1987.) available within a given plant species to improve commercial crop species. This disease resistance which evolved through reassortment of traits via intra-specific crossing and subsequent natural selection, "Single Mendelian traits" (McIntosh, R. A. A catalog of gene symbols for wheat [1983 edition], Proc. 6th Int'l. Wheat Genet. Symp. Kyoto, Japan, 1983, 1197, 1983.) can provide the plant with race-specific resistance to races evolving within a given microbe species. Race-specific resistance is often attributable to a match-up of a single dominant trait in the host with a single dominant trait in the pathogen which is called a gene-foregene interaction (Flor, H. H. Current status of the gene-foregene concept. Annu. Rev. Phytopath., 9, 275, 1971.).

In addition to non-host resistance and race-specific resistance there is the phenomena of induced resistance. Plants which have no genetically definable traits for disease resistance can often generate disease resistance by induced resistance. Induced resistance occurs when a plant, prechallenged by a non-virulent microbe, is subsequently inoculated with a virulent pathogen (Kuc', J. and Preisig, C. Fungal regulation of disease resistance mechanisms in plants, Mycologia, 76, 767, 1984.). As a result, the virulent pathogen is often resisted. Another amazing aspect of induced resistance is the observation that a challenge by a compatible virulent pathogen can also induce a resistance response which retards infection by subsequent inoculation of the same pathogen in adjacent leaves. Induced resistance can also occur following the application of a compound capable of eliciting a disease resistance response (Hadwiger, L A. and Beckman, J. M. Chitosan as a component of pea-*F. solani* interactions. Plant Physiol., 66, 2305, 1980). Often disease resistance does not function properly if metabolic inhibitors (Heath, M. C. Effects of heat shock, actinomycin D, cycloheximide, and blasticidin S on non-host interactions with rust fungi. Physiol. Plant Pathol., 15, 211, 1979.) heat shock, etc. (Chamberlain, D. W. and Gerdemann, J. W. Heat-induced susceptibility of soybeans to *Phytophtophthora megasperma* var. *sojae, Phytophthora cactorum,* and *Hebninthosporium sativum.,* Phytopathology, 5670, 1966.) are utilized to interfere with the development of a resistance response (Hadwiger, L. A. and Wagoner, W. W. Effect of heat shock on the mRNA-directed discase resistance response of peas, Plant Physiol., 72, 553, 1983.). Such observations clearly demonstrate that a plant has the biochemical capability to resist nearly any pathogen if its response is generated both quickly and completely enough to ward off the pathogen.

A definition of non-host resistance in terms of classical genetics, e.g. is not presently possible, because it is seldom possible to make inter-species crosses and follow the chromosomal inheritance of resistance traits within a progeny. However, it is possible to follow genes whose MRNA and protein products accumulate in abundance as non-host resistance is being expressed, Additionally, there is evidence which suggests this specific intense defense response is necessary for disease resistance (Hadwiger, L. A., Wagoner, W. W. Electrophoretic patterns of pea and *Fusarium solani* proteins synthesized in vitro which characterize the compatible and incompatible interactions. Physiol. Plant Pathology 153, 1983.). My laboratory has defined major genes in the pea/*Fusarium solani* f. sp. *phaseoli* interaction which distinguish the resistance reaction from the susceptible reaction between pea and *Fusarium solani* f. sp. *isi*. The cloned response genes of the non-host resistance response and their regulators (promoters) have been transferred to potato plants and been shown to respond quickly and intensely to plant pathogenic stains normally infecting their species.

1. Field of the Invention

The field of the invention is primarily that of genetic improvements of plants through genetic engineering. Ibis invention centers on the use of unique DNA sequences to improve the ability of crop plants to resist diseases.

2. Description of the Prior Art

Conventional plant breeding has been the major and most successful method of improving the disease resistance of crop plants. Genetic traits controlling disease resistance have been identified in plants by genetic crosses which reveal both the distribution of a functional gene (master gene) in gene types and often its location on a chromosome. The first successful engineering of a disease resistance gene occurred when Dr. Ernest Sears of the University of Missouri was able to desegment a chromosomal fragment of a grassy plant and re-associate it with a normal wheat chromosome in an inter-specific cross. The re-associated chromosome piece transferred to wheat a major genetic trait for resistance to a rust-inciting organism. It was realized early that such translocation of chromosome segments often result in the co-transfer of detrimental traits. More recently genetic engineering technology has enabled the transfer of individual genes both within and between plant species.

To date because of the great abundance of repetitive DNA sequences in the region of the plant chromosome which containing the major Mendelian genes controlling discase resistance, attempts to define these major gene DNA sequences have been unsuccessful.

This has generated a second level effort to define genes which become active in a disease resistance response. Some of these genes code for functional proteins such as the enzymes which carry out secondary metabolic pathways in plants (Bailey). There is an abundance of DNA sequence information in the literature for these genes which code for enzymes such as phenylalanine ammonia lyase, cinnamic acid hydrolase, chalcone synthetase and peroxidases (Dixon review). Also, DNA sequences have been obtained for plant structural compounds which increase somewhat after pathogen challenge, for example the hydrolyproline rich proteins. DNA sequences are also available for plant genes which produce hydrolytic enzymes which are capable of degrading individual cellular components of the invading pathogenic organisms. Genes for enzymes such as β-glucanase which degrades β-glucan and chitinase which digests fungal wall chitin have been sequenced and researched extensively. Some or all of these genes probably contribute to the plant's defense. My laboratory has shown that the hydrolytic enzymese β-glucanase and chitinase are capable of releasing from fungal cell walls a small oligomer of chitosan which is capable of suppressing the growth of both virulent and avirulent pathogens for a limited period. However, these compounds appear not to be ultimately determinant in developing complete disease resistance as are the genetic components coding of the enzymes of secondary plant pathways. The major entity of complete disease resistance is cell vitality, in the cells which encircle the point of challenge by the pathogenic organism. In resistance reactions only a few cells in contact with the pathogen lose vitality, whereas in a susceptible reaction a broad radius of cells lose vitality. Paramount to the multiplicity of resistance response associated with plant defense is the speed of the resistance response. Vitality enhancing products must accumulate in cells prior to the appearance of the pathogenic propagule which is releasing its destructive components. The genomic DNA sequences in this invention contain promoters which we have established act rapidly when present inherently in the donor pea. These promoters also act equally well to enhance the output of their associated structural gene products, or when fused with foreign structural genes, enhance other gene products when genetically transferred to a recipient plant species. We have also determined that the product of Gene 49 accumulates in the nuclei of plant cells in the radius of cells which remain viable in a resistance reaction, in an apparent cause and effect relationship.

SUMMARY

The unique DNA sequences have been identified and analyzed from pea plants which contribute to the pea plant's rapid resistance response to an array of plant pathogens including potato pathogens. A method has been described and demonstrated for utilizing the regulatory features of these pea DNA sequences which include AP-1 sites and topoisomerase consensus sites along with their structural genes, for transforming other dicaryotic plants such as potatoes. Transformed potatoes possessing the DNA sequences of the regulatory components of pea genes respond intensively to potato pathogen expressing their vitality gene products. Additionally, the pea regulatory DNA sequences contain A-P-1 binding sites which further increase gene transcription when present with their matching transcription factors. These matching factors can be provided by the co-transformation of DNA sequences of the animal genes fos and jun, to the recipient dicaryote. This molecular transfer of disease resistance traits provides new sources of genetic resistance for transformable crop plants and provides the only means besides natural mutation for genetically improving disease resistance in plants with infertility problems such as potatoes.

BRIEF DESCRIPTION OF THE DRAWINGS

FIGS. 1A-1D. Sequence analysis of the DRRG 49 genomic clone which becomes very actively transcribed in association with "non-host" disease resistance of peas.

The figure includes nucleotide sequence and deduced amino acid sequence of the structural gene of DRRG-PG49 and flanking regions of nucleotide sequence. The consensus sequence known as "TATA" and "CCAAT" boxes are boxed. A polyadenylation signal TAATAAT is also underlined. Repeats are underlined and directions of repeats are indicated by arrows. The sequence consensus to animal or SV40 core enhancer is underlined and denoted with the symbol e. The purine and pyrimidine repeats indicative of ZDNA are overlined and symbolized with z. Potenti consensus sequences for topoisomerase II cleavage sites are underlined and denoted by the symbol t AP-1 sites which are palindromic DNA sequences for attachment of Jun-like or Fos-like transcription factors are denoted by the letter a.

FIGS. 2A-2C. The DNA sequence of the disease resistance response gene of the pea genomic clone designated DRRG-206. This figure includes the predicted protein sequence of the structural gene coded by DRRG-206.

FIG. 3. Schematic representation showing the presumed orientation of the structural gene 49 on a chromosomal loop with the ends of the loop stabilized by the two topoisomerase II consensus sites of the DNA located on 3' and 5' regions attaching to the scaffolding.

FIG. 4. Schematic representation of the transcriptional regulation observed for the expression of the 17 Kd class of near-homologous genes detected with the probe of the structural gene pI49. When the two ends of the loop containing structural gene 49 are attached at the scaffolding, the resulting loop behaves as a circular DNA. The transcriptional control related to conformational changes in the "circular" DNA becomes dependent on the proportion of positive and negative coiling in the vicinity of the RNA polymerase complex which transcribes the gene (upper drawing). In the circular DNAs of prokaryotic organisms the RNA polymerase complex generates positive coils in advance and negative coils in the rear of its progress along the DNA molecule. Thus it is likely that the progress of the RNA polymerase along a chromosomal loop containing a disease resistance response structural gene is influenced by similar alterations in DNA conformation (lower drawing), the most obvious sources of this alteration in coil structure include the topoisomerases which can either gyrase (negative coil) or relax negative coils and all of the external influences by DNA altering compounds. Our evaluations of the accumulation of transcribed MRNA homologous with gene 49 (coding 17 Kd proteins) indicate that compounds which inhibit topoisomerase e.g. novobiocin or N-[4-(acridinylamino)-3-methoxyphenyl]methanesulfonamide (m-AMSA) individually enhance the accumulation of transcript for gene 49 in vivo. The compounds chitosan or actinomycin D which alter DNA directly also enhance transcript accumulation. The two groups of compounds when added in combination synergistically enhance gene 49 transcript.

FIGS. 5A–5D. A schematic representation of how the protein transcription factors from non-plant eukaryotic organisms recognize AP-1 sites (TGACTCA) which can form palindromic structures (Scheme A). The transcription factors Fos and Jun have the potential to form hybrids as they complex with AP-1 sites.

FIG. 5A shows the currently accepted association of Fos and Jun proteins with the DNA sequence TGACTCA or TGAGTCA (AP-1 site) described by Curran and Franza, in Cell. 55:395–397, 1988). Jun forms a hybrid with Fos or another Jun molecule to affect transcription. The more positively charged segments of these proteins associate with the DNA molecule. The "leucine zipper" helix of the Fos protein is more hydrophobic and associates with leucine zipper (L) of the Jun protein.

FIG. 5B proposes that other polymers such as the chitosan heptamer (—C—C—) or other polycationic molecules can augment this association by compensating molecules without regions rich in positive charges.

FIG. 5C proposes in addition that chitosan heptamers can have direct effects on segments of DNA within a chromosomal loop that will influence transcriptions.

FIG. 5D. The lower polymer structure is the chitosan oligomer (heptamer) which constitutes the smallest length of chitosan which will elicit a biological responses in peas.

FIG. 6. Biological observations on nuclear structure which relate to elicitation development of disease resistance. The nuclear anatomy of the plant cell changes following challenge by a pathogen, as a result of these changes new genes are expressed which in the resistance response can preserve the viability (viability production) of many cells, but in the susceptible reaction this viability is lost. The drawing relates how chitosan-like fragments are released from the fungal wall, enter the plant cell and directly or indirectly influence the structure of chromosomal loops and activate host cell responses. The accumulation of the MRNA of disease resistance response genes involved with cell vitality constitute a portion of this response. The accumulation of DRRG-49 gene product (17 Kd protein) in a resistant reaction may benefit the plant cell's vitality.

FIG. 7A and 7B. Summary of the cytological observations of cell vitality in non-host resistance response (upper drawing) over two stages of development in which the vitality is retained in most cells except a few of those directly in contact with the pathogen.

FIGS. 7C and 7D. The lower drawings represent cytological observations of a susceptible reaction in which many cells in the vicinity of pathogen challenge lost vitality allowing fungal growth to resume. The gene 49 transcript which accumulates is much less and the duration of this accumulation is transient, followed by an increase in the growth of the pathogenic organism.

FIG. 8. Relates some standard steps for transforming plants with a defense gene. Pea gene promoter regions (e.g. 5' region and 3' regions of DRRG-49) can be combined in any combination with potentially useful disease resistance or defense genes to transform tobacco by direct transfer to protoplasts (e.g. transient transformation via electroporation) or via Agrobacterium tumefaciens T-1 plasmid (stable transformation). Following regeneration of these cells or tissue to a mature plant, the transformed plant can be tested for successful transfer of disease resistance by pathogenicity tests.

FIG. 9. Results showing pea DRRG-49 promoter segments functioning to activate genes when transferred to tobacco. The DRRG-49 promoter region was connected 5' to the marker gene chloramphenicol acetyl transferase (CAT) in the construction pCC 29. The dot indicated by the arrow represents the accumulation of the product of this enzyme. The CAT enzyme activity was not found in the extract from non-transformed tissue (left lane) but accumulated in the tobacco tissue transiently transformed with this gene construction pCC 29 (right lane). PCaKV CAT is a control induction with a standard promoter (center lane).

FIG. 10. Tobacco tissue when stably transformed with the 5' DRRG-49 promoter driven CAT gene construction (see FIG. 9) produced detectable CAT activity 24 hrs. following challenge with *Fusarium solani* f. sp. *phaseoli* (PHASEOLI) and f. sp. *pisi* (PISI) but not after treatment with water.

TABLE 1

The action of multiple topoisomerase inhibitors synergistically enhancing the accumulation of mRNA for pea gene 49.

Experiment 1.

Influence of novobiocin a topoisomerase inhibitor on the induction of pea gene 49 by actinomycin D and chitosan compounds which alter DNA conformation.

3 μl    1 μl
RNA Accumulation

TABLE 1-continued

The action of multiple topoisomerase inhibitors synergistically enhancing the accumulation of mRNA for pea gene 49.

| Pretreatment 4 hrs | Treatment | Assay I | Assay II |
|---|---|---|---|
| H₂O | H₂O | .75 | .72 |
| Novobiocin 1000 μg/ml | H₂O | 1.76 | 1.11 |
| Novobiocin 500 μg/ml | H₂O | 2.23 | 2.29 |
| Novobiocin 200 μg/ml | H₂O | 1.62 | 1.50 |
| Novobiocin 1000 μg/ml | Actinomycin D 1 μg/ml | 1.87 | 1.35 |
| Novobiocin 500 μg/ml | Actinomycin D 1 μg/ml | 2.47 | 1.61 |
| Novobiocin 200 μg/ml | Actinomycin D 1 μg/ml | 1.98 | 1.32 |
| Novobiocin 1000 μg/ml | Chitosan 60 μg/ml | 2.39 | 3.03 |
| Novobiocin 500 μg/ml | Chitosan 60 μg/ml | 4.63 | 3.30 |
| Novobiocin 200 μg/ml | Chitosan 60 μg/ml | 4.12 | 2.16 |
| H₂O | Actinomycin D 1 μg/ml | .44 | .39 |
| H₂O | Actinomycin D 5 μg/ml | 2.21 | .96 |
| Actinomycin D 5 μg | H₂O | 2.14 | 1.51 |
| Actinomycin D 1 μg | | .32 | .25 |
| H₂O | Chitosan 60 μg/ml | .96 | .72 |
| H₂O | Chitosan 1000 μg/ml | 1.50 | 1.62 |
| Chitosan 1000 μg/ml | H₂O | 2.32 | 1.44 |
| Chitosan 60 μg/ml | H₂O | 1.11 | .75 |

Experiment 2.

The effect of novobiocin or m-AMSA [4'-(9-acridinylamino)methanesulfon-m-aniside) which alter topoisomerases pretreatment on the accumulation of p149 mRNA in peas treated with *Fusarium solani* f. sp. phaseoli, chitosan or actinomycin D.

| Pretreatment μg/ml | Treatment after 1 hr μg/ml | Accumulation of p149 mRNA at 5 hrs % of Control |
|---|---|---|
| H₂O | H₂O | 100 |
| Novobiocin 250 | H₂O | 58 |
| Novobiocin 250 | Actinomycin D 2 | 53 |
| Novobiocin 250 | Chitosan 125 | 182 |
| Novobiocin 250 | F. solani 1 × 10⁶ spores | 100 |
| Novobiocin 125 | H₂O | 76 |
| Novobiocin 125 | Actinomycin D 2 | 64 |
| Novobiocin 125 | Chitosan 125 | 164 |
| Novobiocin 125 | F. solani 1 × 10⁶ spores | 188 |
| H₂O | Actinomycin D | 76 |
| H₂O | Chitosan 125 | 211 |
| H₂O | F. solani 1 × 10⁶ spores | 158 |
| H₂O | H₂O | 108 |
| AMSA 125 | H₂O | 123 |
| AMSA 125 | Actinomycin D 2 | 105 |
| AMSA 125 | Chitosan | 188 |
| AMSA 125 | F. solani | 252 |
| AMSA 250 | H₂O | 117 |
| AMSA 250 | Actinomycin D 2 | 76 |
| AMSA 250 | Chitosan | 200 |
| AMSA 250 | F. SOLANI | 182 |

Pea endocarp tissue (.5 g) was pretreated 4 hrs Exp. 1 or 1 hr Exp. 2 followed by the treatment. The gene 49 specific RNA accumulation was expressed as intensity of x-ray film exposure of a slot blot analyses (Exp. 1) or as a percentage of the control accumulation (Exp. 2). The data indicate that novobiocin and/or mAMSA can enhance alone or synergistically enhance with the elicitor chitosan the accumulation of gene 49 RNA in peas. The effect of the topoisomerase inhibitors is presumably on the chromatin structure within the chromosomal loop containing gene 49.

TABLE 2

The potential control of general plant defense genes by way of influencing the DNA structure of chromosomal loops containing these genes is indicated by the pisatin accumulation data.

| Preliminary[a] Treatment | Secondary Treatment | Pisatin[b] Accumulation μg/g fr. wt. |
|---|---|---|
| H₂O | H₂O | 0 |
| Novobiocin 1 μg/ml | H₂O | 14 |

TABLE 2-continued

The potential control of general plant defense genes by way of influencing the DNA structure of chromosomal loops containing these genes is indicated by the pisatin accumulation data.

| Preliminary[a] Treatment | Secondary Treatment | Pisatin[b] Accumulation μg/g fr. wt. |
|---|---|---|
| H₂O | Chitosan 100 μg/ml | 15 |
| Novobiocin 1 μg/ml | Chitosan 100 μg/ml | 79 |
| H₂O | Actinomycin D (1 μg) | 20 |
| Novobiocin 250 μg/ml | Actinomycin D (1 μg) | 125 |

[a]Pea endocarp were given the indicated preliminary treatment followed 4 hrs by the secondary treatment. The pisatin was extracted in hexanes following 20 hrs of incubation at 22° C.
[b]Pisatin is produced via an isoflavonoid pathway in peas which requires several gene functions to complete this secondary pathway. Pisatin is an antifungal compound. The synergistic influence of novobiocin (inhibitor of topoisomerase a DNA helical effecting enzyme) on the accumulation of pisatin in pea endocarp tissue induced by chitosan (a DNA complexer) and actinomycin D (a DNA intercalater is indicated).

TABLE 3

The accumulation of pea DRRG-49-homologous RNA at 17 hr following treatment of pea endocarp tissue with chitosan-like heptamers from *Fusarium solani* and *Pseudomonas syringae*.

| Treatment | RNA Accumulation % Control | |
|---|---|---|
| | Assay I | Assay II |
| H₂O | .71[a] | .46 |
| Chitosan H.M.W. Shrimp 2 μg/ml | 1.77 | |
| Chitosan H.M.W. Shrimp 1 μg/ml | 2.68 | |
| Chitosan H.M.W. Shrimp .750 μg/ml | 2.76 | |
| *Fusarium solani* f. sp. phaseoli heptamer 1 μg/ml | .78 | .51 |
| Race 1 *Pseudomonas syringae* chitosan heptamer | | |
| 2 μg/ml | 1.35 | 1.30 |
| 1 μg/ml | 2.11 | 1.06 |
| .5 μg/ml | 1.44 | .83 |
| .25 μg/ml | 1.55 | .46 |
| *Pseudomonas syringae* pv. syringae heptamer TN-5 mutant 1 μg/ml | .69 | .50 |
| *Pseudomonas syringae* pv. syringae heptamer | 1.11 | .94 |

[a]Pea pods (.5 g) were split and the endocarp surfaces were treated with the specified chemical and incubated at 22° C. for 17 hrs. Chitosan H.M.W. is high molecular weight (>1 × 10⁶) shrimp shell derived. Heptamers were derived from the indicated pathogens by extraction with proteinase K and sodium dodecyl sulfate. The acetic acid (1%) soluble fraction was fractionated on a FRACTOGEL column to recover an oligomer size of heptamer or larger. Following incubation the gene 49 homologous RNA accumulation was assayed in proportion to the intensity of x-ray film exposure.

DESCRIPTION OF PREFERRED EMBODIMENTS

Figure 3:
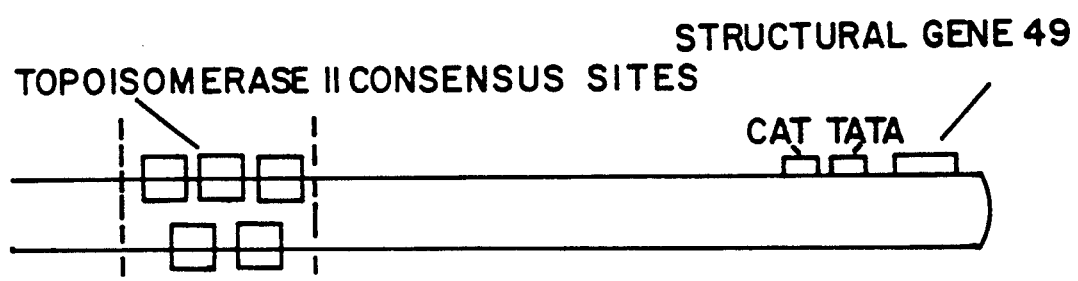
Figure 4:
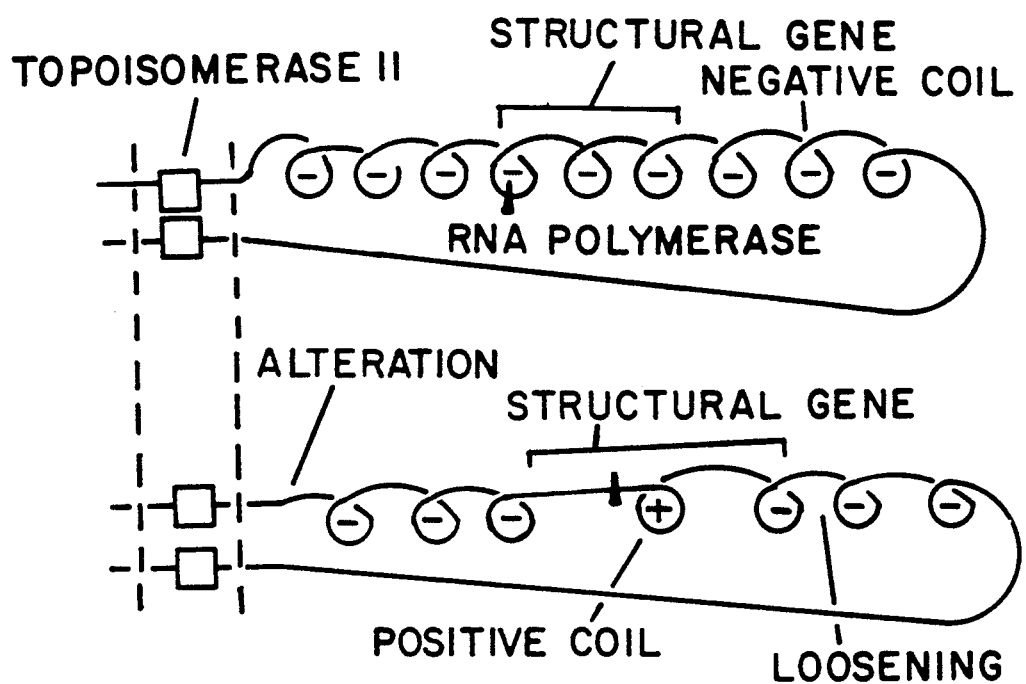
Figure 5A:
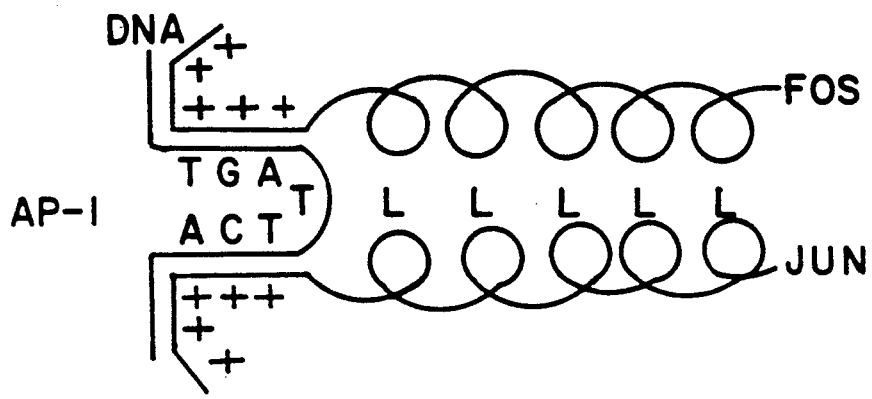
Figure 5B:
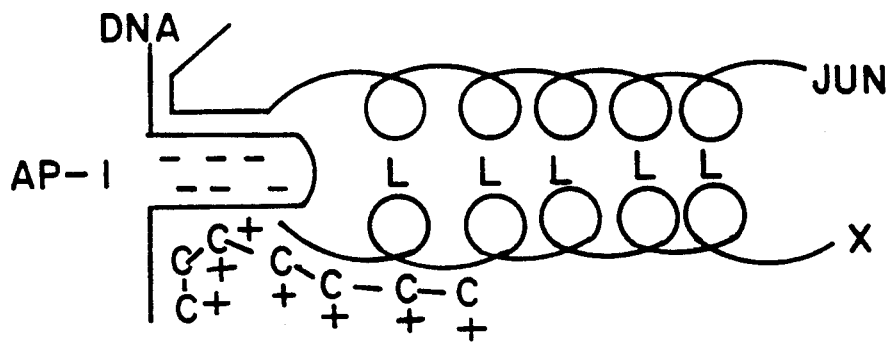
Figure 5C:
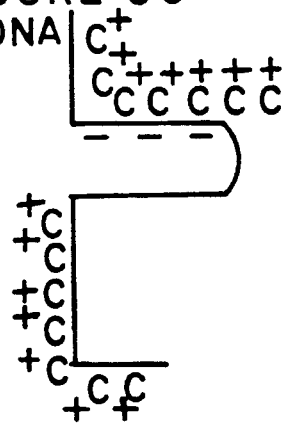
Figure 5D:
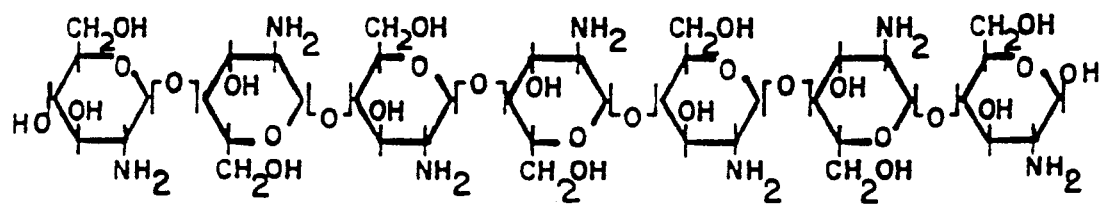

A new genetic base of disease resistance genes is required for the protection of plants from fungal and bacterial pathogens. In the past, this protection for a specific crop species was often available in the world collection of plants of the same or closely related species assembled by government agencies such as the U.S.D.A. plant introduction service. When disease resistance traits were identified in plants within this collection, the plant was crossed with a commercially desirable cultivar of the crop plant, followed by a screening program to select resistant and agronomically desirable progeny from these crosses. The genes which transfer a potential for disease resistance are often controlled by a single Mendelian trait. Since pathogens can often develop the ability to overcome this resistance, the breeders have depleted many of the Mendelian traits which had enjoyed eras of great success. Research in my laboratory indicates that the actual expression of immunity is, in fact, a multigenic response which is in some manner triggered in the presence of the single Mendelian trait (discussed above) for disease resistance. Alternately this multigenic response can be artificially triggered by fungal elicitors in the absence of the Mendelian gene (master gene) or by challenge of the plant tissue by a pathogenic fungus which is incompatible with this plant tissue. For example, if you challenge pea tissues with a fungal pathogen, normally a pathogen of beans, the challenge will activate a response in peas that will provide it immunity to subsequent challenge by the pea pathogen. The resistance of peas to a bean pathogen is termed "non-host resistance." This resistance, which once induced also protects the pea plant from subsequent challenge by the authentic pea pathogen, is called "induced resistance."

This patent will describe a method for transforming dicaryotic plants with DNA sequences from the pea genes which constitute a major fraction of the plant defense response, without dependence on the classical Single Mendelian genes controlling disease resistance (discussed above), which traditionally have been used to transfer disease resistance in plants. Ibis novel approach is based on recent research which has identified a class of DNA sequences from pea (Pea DRRG 49 homologs) that produce proteins in the approximate size range of 17 kilodaltons which we demonstrate are transformable between plants to influence disease resistance. Also we provide representative DNA sequences (AP-1 sites and topoisomerase consensus sites) on the promoter region of gene 49 and/or gene 206 which function in the regulation of these and other genes in transgenic plants.

1. First, some proteins have been identified as major components of non-host resistance. Of those a major 17 KD (kilodalton) protein class is expressed in temporal correlation with the expression of disease resistance. Although the CDNA clones of their genes have been reported in the literature by our laboratory, at that time they were only known to be detectable by probes screened from a CDNA library and were known only as cloned genes among some 300 other clones of genes which were expressed in the disease resistance response of peas.

This patent will describe the sequence analysis of and fundamental aspects of their regulatory regions which will be used to regulate both their own structural genes and other structural genes in transgenic plants.

2. Genomic clones containing key promoter DNA sequences (regulatory sequences) of genes DRRG-49 and DRRG-206 have been obtained as well as the complete DNA sequence analyses. The gene DRRG-49 structural gene can code for the 17 KD major protein. Further, the regulatory regions of DRRG-49 and DRRG-206 have unique sites (DNA sequences) which enable any gene attached in line behind these sequences to be expressed in a foreign plant (e.g. tobacco and potato) in response to challenge by certain bacterial or fungal pathogens. These regulatory sites are included and identified in the sequence analysis of the genomic clones for DRRG-49 and DRRG-206 (FIG. 1 and FIG. 2) and are representative of families of genes which become very actively transcribed in association with "non-host" disease resistance of peas. The DNA sequences and deduced amino acid sequence of DRRG-49 and flanking regions are also shown in FIG. 1. The consensus sequence known as "TATA" and "CCAAT" boxes are underlined. A polyadenylation signal TAATAAT is also underlined. Repeats are underlined and directions of repeats are indicated by arrows. The sequence consensus to animal or SV40 core enhancer is underlined and denoted with the symbol e. The purine and pyrimidine repeats indicative of ZDNA are overlined and symbolized with z. Potential consensus sequences for topoisomerase 11 cleavage sites are underlined.

AP-1 sites which are palindromic DNA sequences for attachment of Jun-like or Fos-like transcription factors.

FIG. 2 presents the DNA sequence of the disease resistance response gene of peas designated DRRG-206 and the predicted protein sequence of the structural gene coded by DRRG-206 DNA sequence. Gene DRRG 206 contains numerous ATATTT or ATATTG have some specificity for chromosome scaffold attachment.

3. Some segments of the regulatory sites of the genomic clone of DRRG-49's 3' and 5' DNA also contain clusters of consensus DNA sequences for recognizing topoisomerase 11, an enzyme found in the nuclear scaffolding of all eukaryotic or assisms. The importance of these DNA sequences resides in their potential to 9 I direct the DNA (foreign to the recipient plant) obtained via genetic engineering techniques from a donor plant to specific hereditable sites in a recipient plant cell. These sequences are recognized as scaffold attachment regions (SAR) or Matrix attachment regions (NUT) (for review see J. W. Newport and Forbes, D. J., 1987, The nucleus: structure, function and dynamics. Ann. Rev. Biochem, 56:535-565.), thus are likely to attach to the recipient cell's nuclear scaffolding and thus experience regulation and expression much as they did in the donor cell. That is they will have a homing device built in so that when transformed into the recipient plant the gene will not be suppressed by attaching to a suppressed area of the chromosome. In the case of the DRRG-49 gene, the two scaffold attachment clusters are likely to cause the placement site of the structural gene to be on a chromosomal loop (FIG. 3). This loop will, when incorporated into a recipient plant, again experience the same regulation in the recipient cell which was dependent, in the donor cell, on torsional stresses within the DNA of the loop. Schematic representation (FIG. 4) of the transcriptional regulation observed for the expression of the structural gene pI49 DNA sequences. When the two ends of the loop containing structural gene 49 are attached at the scaffolding, the resulting loop behaves as a circular DNA. The transcriptional control related to conformational changes in the "circular" DNA becomes dependent on the proportion of positive and negative coiling in the vicinity of the RNA polymerase complex which transcribes the gene. In the circular DNAs of prokaryotic organisms the RNA polymerase complex generates positive coils in advance and negative coils in the rear of its progress along the DNA molecule. Thus it is likely that the progress of the RNA polymerase along a chromosomal loop containing a disease resistance response structural gene is influenced by similar alterations in DNA conformation, the most obvious sources of this alteration in coil structure include the topoisomerases which can either gyrase (negative coil) or relax negative coils and all of the external influences by DNA altering compounds. Our evaluations of the accumulation of transcribed MRNA homologous with gene 49 DNA sequences indicate that compounds which inhibit topoisomerase, e.g., novobiocin or N-[4-(acridinylamino)-3-methoxyphenyl]methanesulfonamide (m-AMSA) individually enhance the accumulation of transcript for gene 49 in vivo (Table 1, Table 2). The compounds chitosan or actinomycin D which alter DNA directly also enhance transcript accumulation. The two groups of compounds when added in combination synergistically enhance gene 49 transcript.

4. The special AP-1 DNA sequences (TGACTCA) or (TGAGTCA) within the DRRG-49 clone are designed to form palindromes within the DNA strand which enables recognition by transcriptional factors (FIG. 5). These transcription factors are usually protein and are coded by genes separate from the genes being regulated. This patent also describes a method utilizing the unique pea DNA sequences for regulating the expression of disease resistance response genes by genetically coordinately controlling the production of specific transcription factors primarily Leucine zipper coding sequences (For review see W. Gruissem, 1990 of fingers, zippers and boxes. Plant Cell, 2:827–828.) which can be derived from any of a large number of eukaryotic organisms. For example, oncogenes such as Fos and Jun which are found in animals can recognize these TGACTCA (or TGAGTCA) sequences. They can also affect transcription of the genes which have AP-1 sites in their regulatory regions. FIG. 5 shows the currently accepted association of Fos and Jun proteins with the DNA sequence TGACTCA or TGAGTCA (AP-1 site) (Curran and Franza. Cell. 55:397, 1988). Jun forms a hybrid with Fos or another Jun molecule to affect transcription. The more positively charged segments of these proteins associate with the DNA molecule. The "leucine zipper" helix of the Fos proteins is more hydrophobic ends associates to form a leucine zipper (L). The co-transfer of genes with "oncogene-like" transcription factors along with desirable genes, under the control of the disease resistance response gene's AP-1-containing regulatory sequences, will affect the expression of the desirable transgenic trait (e.g. the 17 KD proteins).

5. This patent further instructs the user in the method of constructing synthetic signals which work both independently of natural transcription factors and/or in combination with total or partial segments of natural transcription factors inherently present in the recipient plant (FIG. 5). For example, one eukaryotic model for gene regulation described in the literature involves two molecules (for example protein products of fos and jun genes of animal systems) of transcription proteins which combine to form a dimer. The ends of these molecules, which possess DNA affinity, attach to both surfaces of the GTACTCA palindrome while the other ends of the transcription protein self-assemble through hydrophobic regions termed the leucine zipper.

This patent provides procedures for augmenting or substituting for the DNA affinity of the transcription factors described above using hexosamine polymers of comparable size. That is, the genes transferred to the donor are regulated by a seven-plus sugar segment of poly-hexosamine possibly by serving as a bridge between the hydrophobic zipper or similar structure and the palindromic DNA structure (FIG. 5). The positive charges provided by the amino groups on the glucosamine polymer will attract both the $PO_4^-$ groups of the DNA and the negatively charged amino acids within the transcription factor proteins. FIG. 5 proposes that other polymers such as the chitosan heptamer (—C—C—) or other polycatonic molecules can augment this association by compensating molecules without regions rich in positive charges.

FIG. 5 proposes in addition that chitosan heptamers can have direct effects on segments of DNA within a chromosomal loop that will influence transcription (Table 3).

FIG. 5 indicates the structure of chitosan oligomer (heptamer) which constitutes the smallest length which will elicit a biological defense response in peas.

Figure 6:
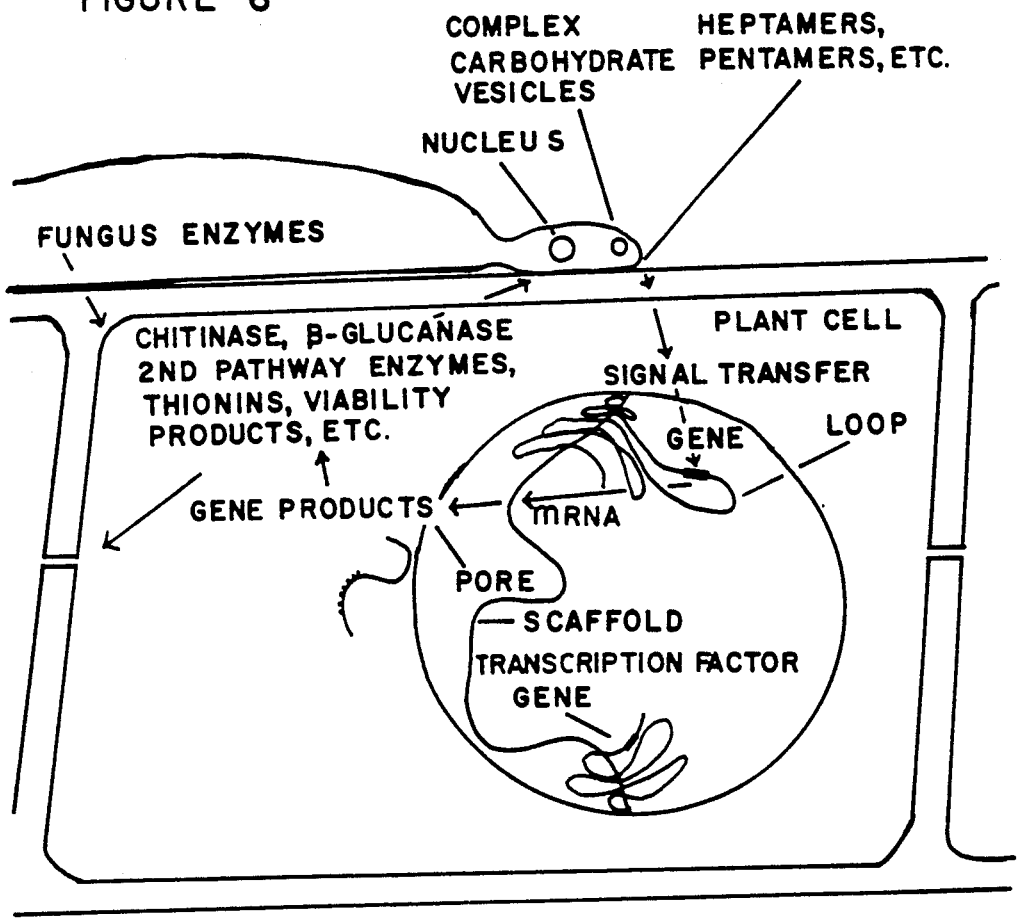
Figure 7A:
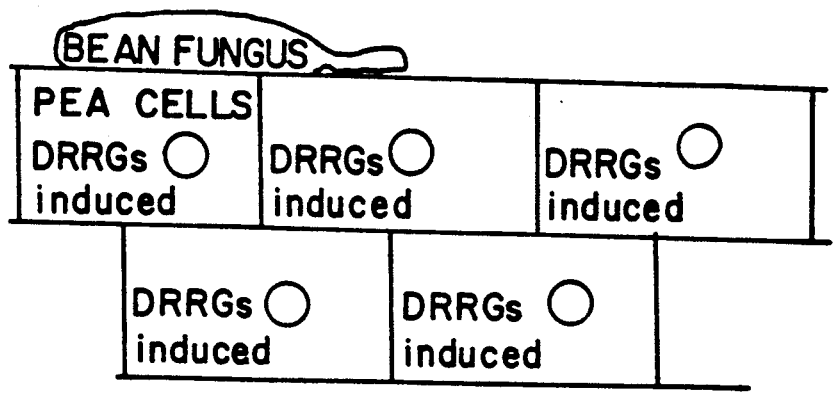
Figure 7B:
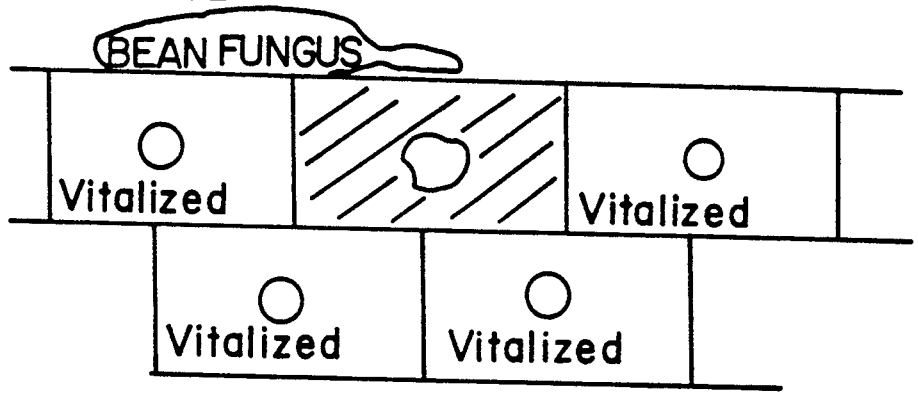
Figure 7C:
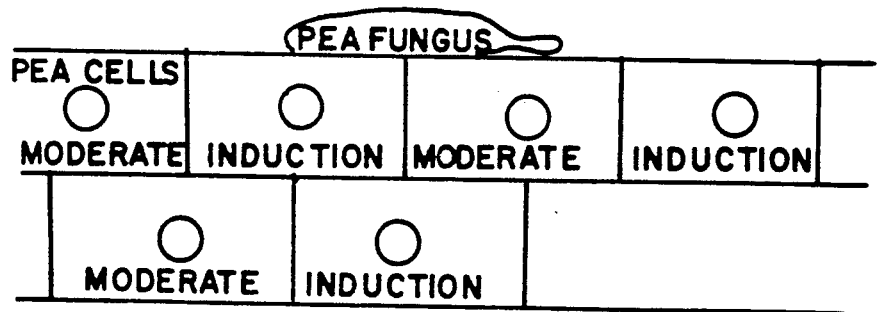
Figure 7D:
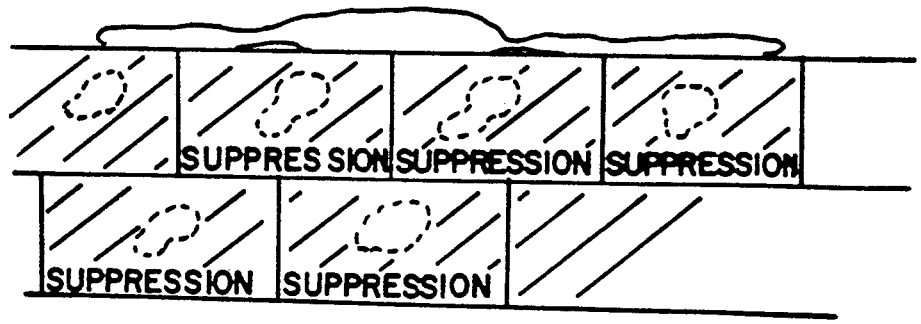
Figure 8:
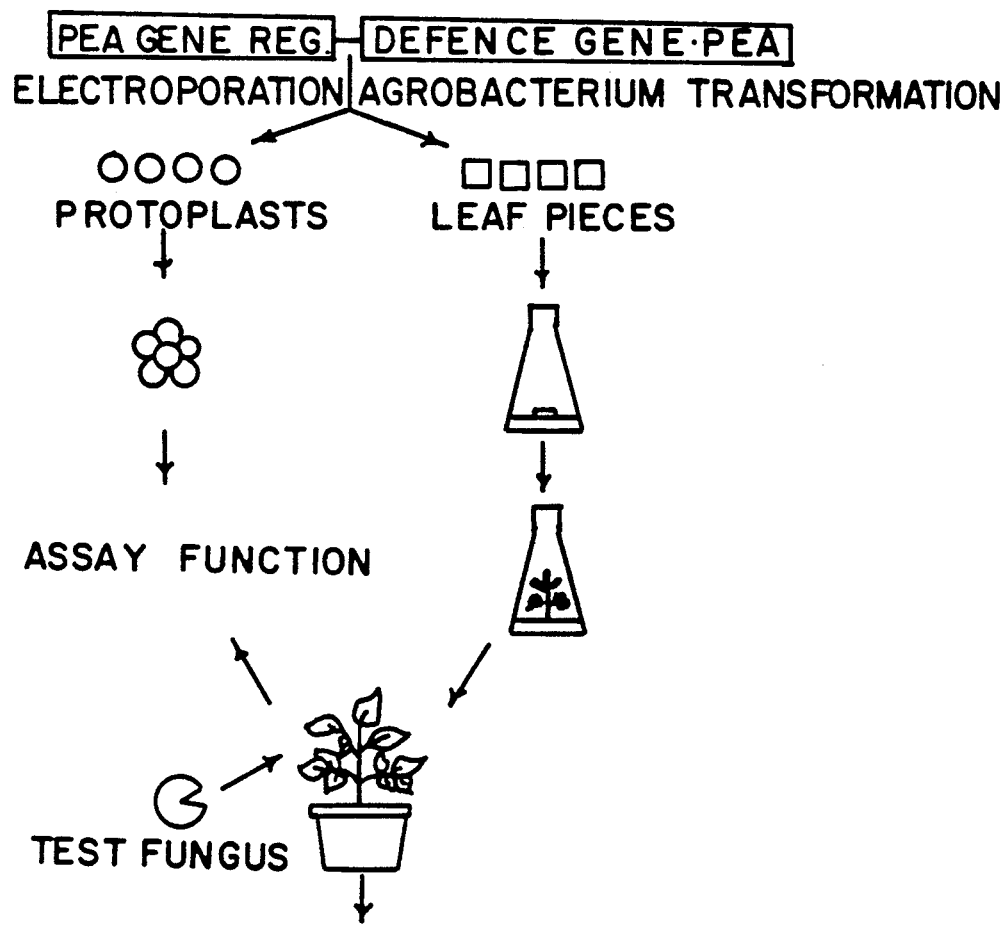
Figure 9:
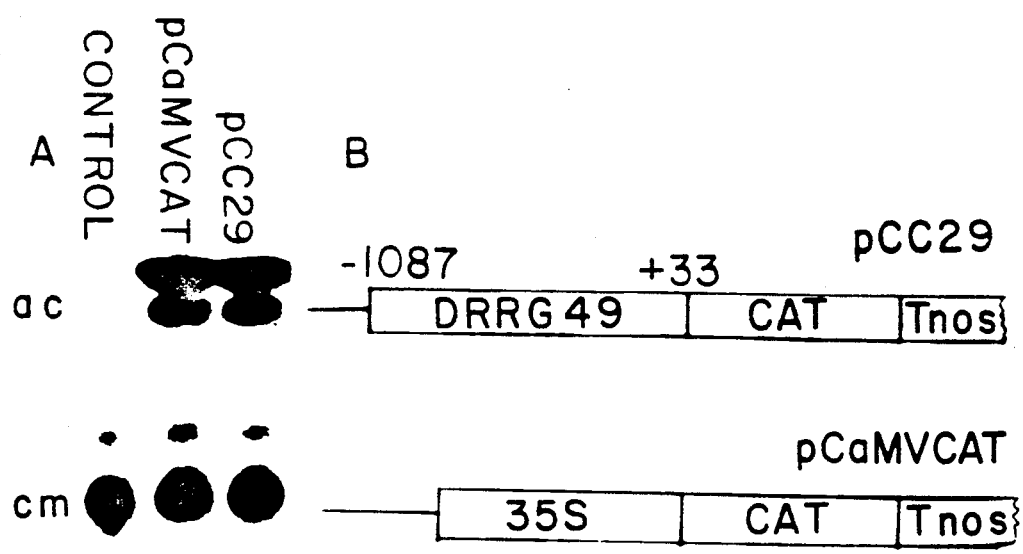
Figure 10:
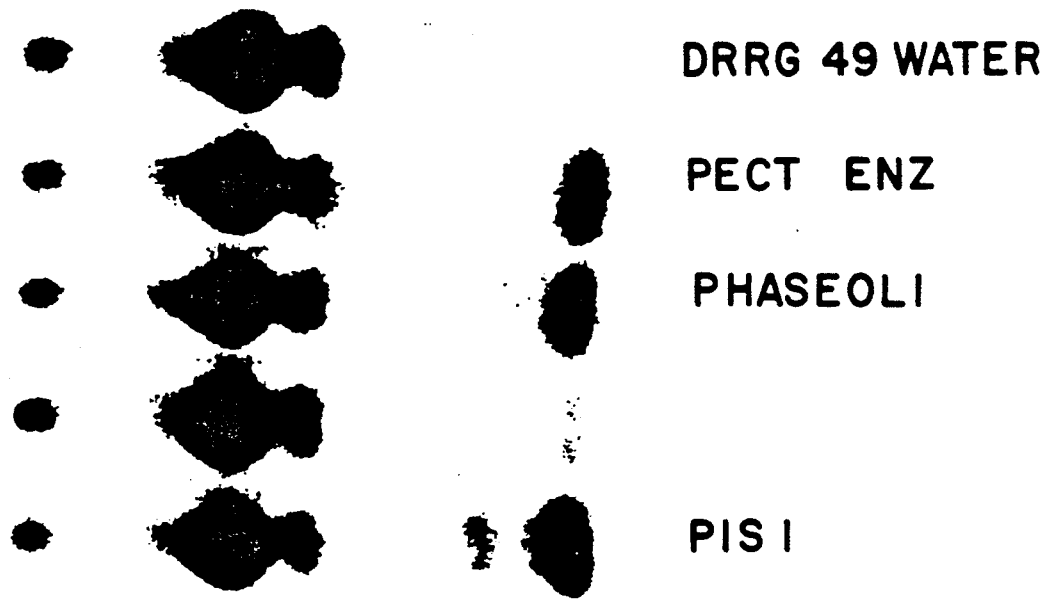

6. The super expression of 17 KD protein of the pea gene 49 DNA sequence appears to enhance the vitality of plant cells in the vicinity of the fungal or bacterial pathogen challenge (viability product FIG. 6). Chitosan-like fragments are released from the fungal wall, enter the plant cell and directly or indirectly influence the structure of chromosomal loops and activate host cell responses. The expression of disease resistance response genes (DRRGS) involved with cell vitality constitute a portion of this response. The accumulation of DRRG-49 DNA sequence product (17 KD protein) in a resistant reaction benefits the plant cells vitality. Although the cell in direct contact with the pathogen can lose vitality and cellular organization, the cells in peripheral regions in resistant tissue retain their vitality (FIG. 7). These cells are highly enriched with accumulations of pea gene DRRG 49 encoded protein. Susceptibility, on the other hand, is associated with a loss of many cells in progressive concentric circles in a direction away from the pathogen challenge. Thus, the concept of this patent for improving disease resistance is unique in light of current concepts that depict disease resistance as a build-up of components toxic to the pathogen, within the vicinity of the challenge. Our strategy is to build up the level of natural plant cell products that protect unchallenged tissue by enhancing cell wall and membrane thickness, reducing fungal product transport, and generally enhancing the structural and functional cellular features by increasing major proteins, such as the 17 KD proteins to maintain cell vitality. The mechanism for controlling this super build-up of 17 KD protein components is by transferring the DNA sequence of DRRG 49 (and DNA sequences of other genes such as DRRG 206 which can further express proteins of this type to the recipient plants. The transferred genes are equipped with regulatory regions of DNA in directions 3' and 5' from the structural gene, which will respond to signals released from the challenging pathogens.

The novel features of this patent are 1) the regulatory regions of the DRRG genes 49 and 206 of peas when attached to any structural gene enables the regulation of this structural gene when challenged by a pathogen formerly compatible with (able to infect) the plant receiving a disease resistance trait. 2) The massive production potential of 17 KD proteins products (FIG. 7 shows the massive accumulation of this product in nuclei after challenge by the pathogen) of these DNA sequences in a plant transformed with DRRG-49 and of DRRG-206 transcript along with the regulatory segments which afford this recipient plant superior disease resistance by maintaining the vitality of cells peripheral to the challenge. 3) The co-transfer of eukaryotic genes (e.g., fos and jun transcription factor genes) for additional transcriptional control into the recipient plant can attain a super production of the 17 KD proteins. In combining these features, the novelty is in constructing a base of disease resistance, independent of the major Mendelian traits traditionally utilized in the past for breeding disease resistance in plants. Finally, a unique complete methodological guide is provided for the transfer and regulation of other non-host resistance traits between plants of different species.

The transfer of genes to recipient plants involves the use of many molecular biological procedures vectors, particle guns, electrical currents, etc., which are generally defined procedures which are no longer novel or unique (For review see T. M. Murphy and W. F. Thompson, 1988. Molecular Plant Development, Prentice Hall, N.J. or Genetic engineering of plants, National Academy Press, Washington, DC, 1984.) These techniques are not a part of the intended patent protection sought. Only the methods for transferring to dicaryotic plants the unique pea DNA sequences DRRG 49 and DRRG 206 which control the encodement of the 49 and 206 structural genes and which are expressed both in their native pea plant and in transgenic dicaryotic plants (tobacco and potato plants) following challenge by plant pathogens, constitute the substance of this invention.

DESCRIPTION OF SECTION NO. 1 OF THE METHOD

Identification of Disease Resistance Response Gene Products Coded by Unique Sequences The sequences of the CDNA clones of pea genes which respond to challenge of the pea plant with a type of plant pathogen has been published and is not claimed as a component of the new and unique method. The sequence analysis of the cloned DNA in itself does not provide a basis for its importance as a disease resistance factor, but provides a link to the identification of one of approximately up to 300 plant genes whose expression is altered following fungal challenge. Of these at least one unique CDNA clone of pI-49 was deemed crucial to disease resistance via an assessment of it being expressed as a major protein that by association assists the retention of cell viability in disease resistant tissue, this assessment has been based on the actual accumulation of new molecules of gene 49 protein in nuclei within the cells retaining viability utilizing rabbit anti-pI-49 pea protein antisera (FIG. 7).

Thus this patent instructs that the gene-49-like pea proteins, more than other individual genes (of the 300 plant genes altered), are useful in plants for assisting disease resistance.

DESCRIPTION OF SECTION NO. 2 OF THE METHOD

Genomic Clones DRRG-49 and DRRG-206

The genomic clones of gene disease resistance response gene (DRRG)-49 and DRRG-206 contain DNA both to the left (5') and to the right (3') of the genetic information for coding the 17 kilodalton protein (DRRG-49). The process for obtaining and sequencing this genomic DNA is not unique or new, but these left and right regions contain regulatory components unique for the induction of these genes at the time resistance is expressed.

Sequences of selected genomic clones of DRRG-49 and DRRG-206 are presented in FIGS. 1 and 2.

DESCRIPTION OF SECTION NO. 3 OF PROCESS

Topoisomerase II Consensus Sites and Their Utilization in Scaffold Recognition The topoisomerase II consensus sites have been identified on DRRG-49 (see FIG. 1). They occur in clusters at the extremities of the left hand (5') and right hand (3') regions from the structural gene sequenced from this genomic clone. We have established that these regions complex with the scaffolding isolated from pea nuclei. This strongly suggests that these consensus sites in these pea genes 49 functions as do the general consensus of other eukaryotic organisms (for review see Adachi, Y. et. al. 1989. Preferential, cooperative binding of DNA topoisomerase II to scaffold associated regions EMBO J. 8:3997–4006) to attach specifically to the nuclear scaffolding specifically at this sequence. Also gene 206 (FIG. 2) contains numerous ATATTT or ATATTG sites which have some specificity for the scaffold C)C therefore when segments with these sequences are transformed to tobacco, potato or other plants the DNA will logically insert in the region of the scaffold and be subject to regulation similar to that regulation it experienced when in the pea genome.

Further a portion of this regulation is dependent on this genomic segment existing as a loop. That is the regulation of the gene which is controlled by torsional stress, helical state or chromatin conformation will be related to changes in helicity occurring because the DNA loop is stabilized at two ends. It has been established in prokaryotic systems that when the RNA polymerase complex moves in a 5' to 3' direction on a circular DNA that there is generated a positive helicity in front and a negative helicity in the rear of its advance. All of the factors which enhance or detract from this helicity flux, moderate the rate of transcription. We have established that the accumulation of MRNA from the pI-49 gene can be influenced by altering the function of topoisomerase II (the component of the scaffold which holds the topoisomerase II specific DNA sequence), altering the conformation of the loop by DNA specific components (some of which are signal compounds released by the invading pathogen) and by an compounds which influence topoisomerase I which is associated with reduction of the negative helicity of DNA (Tables I and II).

In summary the topoisomerase II consensus sites are necessary components for some non-host defense genes which are needed 1) to properly localize the insertion of the genomic clone into the genome of the recipient plant and 2) to properly regulate the gene expression following transformation as the plant is defending itself from the pathogen.

DESCRIPTION OF SECTION NO. 4 OF THE METHOD

AP-1 DNA sites within disease resistance response genes

Two AP-1 sites (TGACTCA) and (TGAGTCA) have been discovered within the pea genomic clone DRRG-49. My laboratory has shown that segments containing these sequences complex with the product of the oncogene protein "Jun" in a manner similar to that in other eukaryotic organisms in which regulatory regions of some genes containing AP-1 sites associate with Jun and other oncogene specific proteins (e.g. fos) functioning as transcription factors.

In the process of transferring non-host resistance of peas and other genes to other plant species, the AP-1 site and other receptor sites can serve as auxiliary regulatory sites. In the same way that protooncogenes when converted to a highly transcribed oncogene enhance the activity of numerous genes in a tumorous tissue, the co-transformation of oncogenes with non-host disease resistance genes containing an AP-1 site can enhance the transcription of these plant genes.

DESCRIPTION OF SECTION NO. 5 OF PROCESS

Other workers have shown that the oncogene products Fos and Jun can form hybrids which 1) recognize the palindromic sequence TGACTCA by virtue of DNA binding sites and 2) recognize each other because of the hydrophobic association of their leucine containing helicies called their "leucine zippers" (FIG. 5) (for review see Schuermann, M. et. al. 1989. The leucine repeat motif in Fos protein mediates complex formulation with Jun/AP-1 and is required for transformation. *Cell* 56:507-516). Ibis complex does not always constitute a hybrid. Two Jun molecules can complex an AP-1 site alone, however two Fos molecules require assistance for the DNA complexing function. Our investigations of the DNA complexing properties of the carbohydrate chitosan indicate chitosan and other polycatonic polymers should augment the DNA binding of Fos-like transcription factors (FIG. 5) to these AP-1 sites.

In summary AP-1-like sites (palindromic sites) native to genomic clones of non-host resistance genes and others to be constructed and inserted into these genes can be utilized in the regulation of these genes when transformed to a recipient plant. The construction can be tailor-made to recognize native "Jun-like" transcription factors. Also the deficiencies of native transcription proteins in recognizing this palindromic DNA can be 1) augmented by the supplementation to the plant of "chitosan-like" polymers or 2) contributed by the invading pathogen itself.

DESCRIPTION OF SECTION NO. 6 OF THE METHOD

The central feature of both non-host disease resistance and the race-specific resistance obtainable by the transfer of specific Mendelian traits within a species, is the maintenance of cell viability in the host plant tissues surrounding the pathogen challenge. The family of 17 KD proteins synthesized by legume plants (via DRRG 49-like DNA sequences) is a component of this viability, based on the enhanced appearance of this protein in a non-host resistance response (FIG. 6), especially in the heterochromatin of the nucleus of cells which retain viability.

Although the pea clone pI-49 was one of many described previously in published reports, the recent discovery that this clone encodes for a protein of the KD-17 type and instructs that these are major proteins produced in the non-host resistance reaction. Thus the clone DRRG-49 and a family of other genomic clones which can be recovered from a pea genomic library using the pl-49 probe, are important traits which are likely central to the development of non-host resistance. Further many plants have DNA segments which share some homology with pl-49 and yet lack disease resistance against pathogens readily resisted by pea tissue containing these genes. We interpret this to mean that it is the regulation of, rather than simply the possession of the gene trait alone, which is important and have developed this novel process of transferring regulated non-host disease resistance on this condition.

A final feature of the transfer and regulation of non-host resistance in a recipient crop plant is the use of non-protein-coding portions of the DRRG-49 and other disease resistance response genes in the regulation of other functional genes which could influence the intensity of the resistance response. For example we have found that the pea enzymes chitinase and $\beta$-glucanase can attack the *Fusarium solani* f. sp. *phaseoli* fungal cell wall and cause the release of chitosan fragments which at 7 ppm can readily stop the growth of this fungal pathogen. The up regulation of chitinase and $\beta$-glucanase gene transformation following pathogen challenge may well intensify the disease resistance response in the recipient plant transformed with DRRG-49 promoter segments in front of the chitinase and $\beta$-glucanase structural genes. This strategy is instructive in that we have discovered that chitinase and $\beta$-glucanase suppress fungal growth indirectly by release of the antifungal wall fragments (chitosan) rather than directly by stopping the growth of the fungus by cell lysis via cell wall destruction.

The DRRG-49 promoter segments may also be placed in line with genes controlling secondary metabolism pathways which produce antifungal and antibacterial genes.

DESCRIPTION OF FEATURES OF THE METHOD WHICH ARE NOT NEW OR NOVEL BUT ARE NECESSARY TO PERFORM THE MECHANICS OF TRANSFERRING THE NON-HOST RESISTANCE GENES FROM DONOR TO PLANT RECIPIENT ARE GIVEN IN FIG. 8

The example provided FIG. 8 diagramatically shows a typical strategy for transforming, regenerating and pathogen-testing of potato plant. Pea gene promoter regions (e.g., 5′ region and 3′ regions of DRRG-49) can be combined in any combination with potentially useful disease resistance or defense genes by direct transfer to propoplasts (e.g., transient transformation via electroporation) or via Agrobacterium tumefaciens T-1 plasmid (stable transformation). Following regeneration of these cells or tissue to a mature plant it can be tested for successful transfer of resistance by pathogenecity tests. Many other transformation mechanistic strategies will obtain the same result.

PROCEDURE FOR DEVELOPING, TRANSFERRING AND AUGMENTING NON-HOST RESISTANCE IN TRANSGENIC PLANTS

1. Select multiple plant species and multiple plant pathogenic organisms which have defined host ranges within the selected plant species. Since, in nature, a given pathogenic organism (e.g. pathogen "X") has adapted evolutionarily to one or a few plant species, it cannot destructively infect plant species (Host A) out of its narrow host range. Thus Host A can express non-host resistance to plant pathogen "X". This plant species, Host A, is now the source of non-host resistance gene DNA sequences which, when transferred and regulated within the dicotyledonous plant species Host B (within the host range of pathogen "X") and normally infected by pathogen "X", is now rendered resistant.

2. Non-host resistance genes are identified in Host A by screening a CDNA library of all genes expressed in a non-host resistance reaction for those most highly expressed (in temporal correlation with the expression of resistance) over the expression observed in non-infected tissue.

3. Specific DNA sequences from the disease resistance response genes (DRRG) cloned in No. 2 are utilized to probe for larger segments of the host plant A genome (namely, a genomic library). These genomic clones are now sequenced. The instructive feature of this sequencing is to continue in directions 5' and 3' from the structural genes until topoisomerase II consensus sequences are located. The generalized eukaryotic consensus sequence is (N=any base). We instruct that clusters of plant sequences such as those in pea DRRG 49:

GTCAACATTTCTCCA
ATATAAATTGATGAT
GTATACATTTGTCCA or sequences with less than three errors e.g. GTTTTGGTNAATAAA and GTAAACCATTGAAATG from those of the eukaryotic consensus site will constitute scaffold attachments.

If sequencing of the genomic clone 5' and 3' regions of other defense genes fails to detect these scaffold attachment regions, synthesized or substituted topoisomerase II consensus sequences must be constructed on the extremities of the gene to be transferred to insure site (scaffold)-directed or stable transformation of the donor plant with the gene being transferred.

Within the border regions defined by the topoisomerase II consensus clusters will also reside the AP-1 site sequences TGACTCA or TGAGTCA.

Within the AP-1 sites, but somewhat distal to the CAT and TATA boxes (required to initiate transcription), will be other sequences important for the transient expression of the transformed genes (e.g. see sites in 5' region of DRRG-49). Such sights are still likely to be inadequate for super induction of stably transformed genes.

4. Reporter (marker) genes may now be utilized with these constructs. This will enable the evaluation of the expression of the construct in Host B following fungal challenge. (This step is optional). See FIGS. 9 and 10 for data showing marker expression directed by the 5' regions of DRRG-49. Upper blotch in FIG. 9 is the product of the CAT enzyme produced in tobacco after the DRRG 49 promoter-driven CAT gene was transferred by electroporation. FIG. 10 shows the same CAT enzyme expression in when the DRRG-49 promoter driven CAT gene is transferred to tobacco via the Agrobacterium T-1 plasmid, note that is only expressed when transformed tissue is challenged with pathogen (PISI) pathogen (PHASEOLI) or pathogen extract (PECT ENZ).

5. If the evaluation of the marker constructs is positive, the original construct with the intact structure DRRG is prepared for transfer to the recipient Host B.

6. The procedure can utilize for example DRRGs from peas which resist *Fusarium roseum,* a pathogen of potatoes which can be transferred to potatoes which are destructively infected by *Fusarium roseum.*

7. The native pea gene (DRRG-49) with the addition of an antibiotic selective marker, can be transferred to potato via the Agrobacterium tumefaciens Ti plasmid. Also, within the same plasmid can be inserted the structural pea gene for β-glucanase (and/or chitinase), which contains essentially the 3' and 5' regions of DRRG-49 minus the DRRG-49 structural gene. Other genes which can augment the transcription of these genes can also be included, e.g. the oncogene-like genes (Fos and Jun) coding for AP-1 specific proteins (see No. 9 below).

8. Potato tissues positively transformed are regenerated to mature plants. The plants are evaluated for disease resistance to *Fusarium roseum* and other potato pathogens, for the expression of the transferred genes and evaluated for the rates and levels of β-glucanase (or other hydrolytic enzymes) accumulation following pathogen challenge.

9. Plants with inadequate levels of expression of the transferred genes are subsequently transformed with eukaryotic genes such as Fos and Jun which are animal genes recognizing and regulating genes (such as DRRG-49) with the AP-1 sites as described above.

10. Since transcription of genes contained within the chromosomal loop structures (made possible by the topoisomerase consensus clusters) are also subject to the torsional stresses of the loop, transformed plants are treated with DNA influencing compounds and/or topoisomerase inhibitors to determine if further regulation of transcription is possible in the transformed plants (Table 1, Table 2).

11. Some DNA influencing components are extractable from pathogen walls. Chitosan heptamers and closely related heptamer fragments from fungal and bacterial walls are DNA specific and can be released as signals, presumably influencing the conformation of DNA directly or indirectly. These components can also be utilized to evaluate and augment gene expression in the transformed potato tissue.

CONCLUDING REMARKS

The successful transformation of potatoes described above can also result in the expression of pea β-glucanase in the potato tissue in response to fungal challenge. The transgenic β-glucanase, along with an inherent low level of potato β-glucanase and chitinase, will contact the fungal wall, which is composed of β-glucan and chitin, causing wall degradation. The wall degradation is accompanied by the release of β-glucan and chitin fragments and, more importantly, chitosan fragments. Chitosan is produced as a deacetylated product of chitin. Chitosan, which readily induces DRRG-49 and DRRG-206, will provide a major signal for inducing genes constructed with DRRG-49 and DRRG-206 regulatory sequences.

Also the induction or super induction of co-transferred genes DRRG-49 and DRRG-206 will increase the 17 KD products of DRRG-49 or DRRG-206 which will add a vitality to uninvaded potato cells near infected tissue and thus provide a higher level of disease resistance against potato pathogens.

What is claimed is:

1. The 5' DNA promotor sequence of the DRRG-49 gene of FIG. 1 consists of nucleotides −1084 to +30 which contains the AP-1 binding site sequence, an SV-40 core enhancer sequence and topoisomerase II cleavage sequences.

* * * * *